United States Patent [19]

Shaffer et al.

[11] Patent Number: 5,049,132
[45] Date of Patent: Sep. 17, 1991

[54] BALLOON CATHETER FOR DELIVERING THERAPEUTIC AGENTS

[75] Inventors: Maureen A. Shaffer; James E. Leone, both of Miami, Fla.

[73] Assignee: Cordis Corporation, Miami Lakes, Fla.

[21] Appl. No.: 461,648

[22] Filed: Jan. 8, 1990

[51] Int. Cl.⁵ .......................................... A61M 29/00
[52] U.S. Cl. ..................................... 604/101; 604/96; 606/194
[58] Field of Search .................. 604/96, 101, 280; 128/207.15; 606/192, 194

[56] References Cited

U.S. PATENT DOCUMENTS

| | | | |
|---|---|---|---|
| Re. 32,348 | 2/1987 | Pevsner | 604/194 |
| 3,173,418 | 3/1965 | Baran | 128/207.15 |
| 3,888,249 | 6/1975 | Spencer | 604/280 |
| 4,338,942 | 7/1982 | Fogarty | |
| 4,423,725 | 1/1984 | Baran et al. | 128/207.15 |
| 4,636,195 | 1/1987 | Wolinsky | |
| 4,704,111 | 11/1987 | Moss | 604/280 |
| 4,711,251 | 12/1987 | Stokes | |
| 4,820,349 | 4/1989 | Saab | 604/96 |
| 4,821,722 | 4/1989 | Miller et al. | |
| 4,824,436 | 4/1989 | Wolinsky | |
| 4,946,466 | 8/1990 | Pinchuk et al. | 604/96 |
| 4,994,033 | 2/1991 | Shockey et al. | 604/101 |
| 5,002,531 | 3/1991 | Bonzel | 604/96 |

FOREIGN PATENT DOCUMENTS 8912478 12/1989 PCT Int'l Appl. ............... 604/104
2153675 8/1985 United Kingdom .

OTHER PUBLICATIONS

Article by Wolinsky et al. entitled "Use of a Perforated Balloon Catheter to Deliver Concentrated Heparin Into the Wall of the Normal Canine Artery", Journal of the American College of Cardiology vol. 15 No. 2 pp. 475-481 (Feb., (1990)).

Primary Examiner—John D. Yasko
Assistant Examiner—Anthony Gutowski
Attorney, Agent, or Firm—Gerstman & Ellis, Ltd.

[57] ABSTRACT

A balloon catheter comprises a catheter shaft which typically defines a first inflation lumen and a first, inflatable balloon mounted on the shaft in communication with the first inflation lumen. By this invention a second inflation lumen is typically provided, spaced from the first lumen and defined by the catheter shaft. A second balloon is mounted on the shaft in communication with the second inflation lumen. The second balloon defines apertures which are sized to permit liquid flow outwardly through the balloon. Thus, medication may be delivered in a controlled manner. Alternatively, the second balloon for medication administration may be the only balloon present on the catheter.

13 Claims, 1 Drawing Sheet

BALLOON CATHETER FOR DELIVERING THERAPEUTIC AGENTS

BACKGROUND OF THE INVENTION

As described in Wolinsky U.S Pat. No. 4,824,436, the process of treating coronary artery disease with an balloon (typically the PTCA procedure) results in at least a temporary, forcible expansion of a coronary artery cross section which is narrowed by an atherosclerotic lesion or stenosis. However, following such rough, physical balloon expansion of such a stenosis, often a restenosis takes place in which the artery again closes up. To counter this, heparin is given to the patient. For example, it is the current custom in a PTCA procedure to deliver by injection up to about 10,000 units of heparin as a bolus during or immediately after the procedure, with hourly, additional doses of heparin being administered up to 24 hours after the PTCA procedure. This, however, has known disadvantages in that some patients such as ulcer patients or patients with high blood pressure are contraindicated for the administration of such large amounts of heparin.

As another approach to the problem of restenosis, the previously cited Wolinsky patent teaches the administration of heparin by means of a special catheter to the stenosis area after a PTCA procedure or the like. However, this requires the insertion of a second catheter into the patient's arterial system, to accomplish this special application of heparin In Rowe pending U.S. Pat. Application No. 322,929, filed Mar. 14, 1989 and entitled Method and Apparatus for Delivery of Therapeutic Agent, a balloon catheter is described, being, if desired, of a type useful for a PTCA or related procedure. However, as an improvement, a coating of heparin or other medication is carried on the surface of the balloon. Accordingly, heparin or other medication is forced into the stenosis site by the pressure of the expanding balloon, so that the heparin is applied in a single step as the stenosis area is physically expanded by the balloon. However, there may be a need for larger quantities of medication than can be provided by such an expansion balloon surface as described in the above-mentioned patent application. Additionally, there may be a need for a sequence of medications, to be applied one after the other, and this also is not readily accomplished in the cited patent application with a single catheter insertion. Additionally, it may be desired to apply the medication without the application of substantial pressure, and this also is not done with ease in the above-described invention. Also, there is a need for a system in which the medication does not leak out of the system until the catheter is positioned at exactly the desired location, and where the choice of medication may change with a late decision by the physician after the catheter has been emplaced.

By the invention of this application, any or all of the above objectives may be accomplished, to provide greater flexibility and effectiveness to catheters for delivering therapeutic agents.

DESCRIPTION OF THE INVENTION

In this invention, a balloon catheter is provided which comprises a catheter shaft and an inflation balloon carried thereon in communication with an inflation lumen extending through the catheter. By this invention, the inflation balloon defines aperture means extending through its wall, said aperture means being sized to permit pressurized flow of medication outwardly through the balloon wall. Thus, after proper emplacement of the catheter, the desired medication may be applied to the appropriate site in the body by being forced through the inflation lumen to the interior of the catheter balloon. From there, the medication, typically under at least gentle pressure, migrates through the aperture means of the balloon wall into the desired area for medical treatment.

Specifically, such a balloon catheter may be used for PTCA or other, similar procedures for enlarging arteries and the like, but it may be used for any other purpose as well, such as in a Foley Catheter for the bladder For example, antibiotics may be administered, or anestetic prior to catheter removal. The preferred plurality of apertures on the balloon may be proportioned to be small enough so that the balloon may be pressure-inflated despite the presence of the apertures, while medication flows out of the apertures. Thus, the medication may be forcefully administered by pressure in the expanding balloon, to provide pressure administration of heparin or the like to a stenosis site, for example. In this circumstance, the medication itself serves as the balloon inflation fluid, being administered in a volume and at a pressure so that the balloon is expanded at a desired pressure despite the leakage of medication through the apertures in the balloon wall.

Preferably, the balloon catheter of this invention comprises a catheter shaft which defines a first inflation lumen and carries a first, inflatable balloon which is typically aperture-free. The inflatable balloon is mounted on the catheter shaft in communication with the first inflation lumen.

In accordance with this invention, a second lumen, spaced from the first inflation lumen, is defined by the catheter shaft as well. A second balloon is mounted on the catheter shaft in communication with the second lumen defined in the shaft, this being the balloon which defines the aperture means through its wall as described above. Such apertures of the aperture means are sized to permit liquid flow outwardly through the balloon. Optionally, when the apertures are holes having a diameter of about 0.002 inch or less, many liquid medications will not flow through the apertures except under substantial pressure, which facilitates the inflation of the second balloon with such medication and the administration of controlled quantities thereof at desired pressures. Otherwise, the apertures may preferably have diameters of about 0.01 to 0.05 inch or more for essentially spontaneous medication flow therethrough.

As a further preferred feature of this invention, the second balloon is positioned generally radially outwardly about the first balloon in telescoping relation therewith. Accordingly, pressure from the first balloon can be used to outwardly expand the second balloon, and to help provide pressure administration of the medication, which may flow into the region between the first and second balloons and outwardly through the apertures in the second balloon wall. Accordingly, such a catheter may be used in a PTCA procedure to provide a conventional high pressure expansion of the stenosis site with the first balloon, after the catheter has been properly emplaced. This may be followed by deflation of the first balloon to any desired degree, and the addition of medication such as heparin solution to the area between the first and second balloons through the second lumen, from where the heparin flows outwardly through the apertures, while any desired pressure is administered by any combination of pressurization of the medication itself and the first balloon.

Thus, by means of a single balloon catheter insertion, a PTCA or other balloon expansion procedure may be performed, followed by the immediate administration of any desired medication. The choice of medication may be delayed by the physician until the outcome of the PTCA procedure has been determined. Then, the desired medication solution or combination of solutions may be administered through the proximal end of the catheter through the second lumen into the space between the two balloons, followed by dispersion of the medication at the desired site, under any desired pressure. Alternatively, the balloon catheter for delivering therapeutic agents may be used subsequent to any conventional PTCA or similar procedure to infuse such therapeutic agent without the use of this device to effect dilation of the vessel, or even in cases in which there is no vessel dilation The second, outer balloon may, if desired, not completely overlap the first, inner balloon. For example, when the second balloon has at least a small, proximal section which does not overlap the second balloon, that may serve as a place where the second lumen can communicate with the space within the second balloon and outside of the first balloon.

It may also be desirable for the second balloon to be spot-sealed to the first balloon in a plurality of spaced areas. This facilitates the collapsing of the second balloon, along with the first balloon, by a conventional vacuum suction process for packaging of the catheter. Otherwise, the presence of the apertures in the second balloon makes the suction collapsing of the second balloon to remove all possible air a more difficult process.

The catheter of this invention may also carry a guide wire in its own added lumen, to facilitate the insertion of the catheter of this invention in a manner which is conventional to the clinical catheter art, particularly angiographic and angioplastic catheters.

It may also be desired for the apertures of the second balloon to comprise slits in the second balloon wall having abutting sides in their normal, unstretched configuration, rather than holes with sides that do not normally abut. This limits fluid communication inwardly or outwardly through the wall of the second balloon as the second balloon is collapsed for packaging and then advanced to a desired site in a patient. However, upon even low pressurization, the slit-type apertures open by stretching for the easy delivery of medication to the exterior of the second balloon, and they close again when the pressure ceases.

Examples of medications that may be administered may include any medication or therapeutic agent which would be desirably applied locally to a specific, internal tissue site which is accessible by the catheter.

Specific examples of such medications or therapeutic agents include anti-thrombogenic agents or other agents for suppressing stenosis or late restenosis such as heparin, streptokinase, urokinase, tissue plasminogen activator, anti-thromboxane $B^2$ agents, anti-B-thromboglobulin, prostaglandin E, aspirin, dipyridimol, anti-thromboxane $A_2$ agents, murine monoclonal antibody 7E3, triazolopyrimidine, ciprostene, hirudin, ticlopidine, nicorandil, and the like. Anti-platelet derived growth factor may be used as a therapeutic agent to suppress subintimal fibromuscular hyperplasia at an arterial stenosis site, or any other inhibitor of cell growth at the stenosis site may be used.

The therapeutic agent also may comprise a vasodilator to counteract vasospasm, for example an antispasmodic agent such as papaverine. The therapeutic agents may be vasoactive agents generally such as calcium antagonists, or alpha and beta adrenergic agonists or antagonists. Additionally, the therapeutic agent may include a biological adhesive such as medical grade cyanoacrylate adhesive or fibrin glue, for example to adhere an occluding flap of tissue in a coronary artery to the wall, or for a similar purpose.

Also, the balloon catheter of this invention may be expanded to apply a stent to the coronary artery or elsewhere. With the application of the stent, an anti-thrombogenic agent may be applied to its internal tissue site for preferably long term suppression of thrombogenic activity in the vicinity of the stent.

Additionally, the therapeutic agent in accordance with this invention may be an anti-neoplastic agent such as 5-fluorouracil or any known anti-neoplastic agent, preferably mixed with a controlled release carrier for the agent, for the application of a persistent, controlled release anti-neoplastic agent to a tumor site.

The therapeutic agent may be an antibiotic which may be applied by this invention, preferably in conjunction with a controlled release carrier for persistence, to an infected stent or any other source of localized infection within the body. Similarly, the therapeutic agent may comprise steroids for the purpose of suppressing inflammation or for other reasons in a localized tissue site.

The therapeutic agent may constitute any desired mixture of individual pharmaceuticals of the like, for the application of combinations of active agents.

Additionally, glucocorticosteroids or omega-3 fatty acids may be applied, particularly to stenosis sites to obtain clinical benefit thereby. Any of the above medications may include controlled release agents to prolong the persistence of the medication.

Thus, by this invention, medications may be applied in conjunction with a pressure-applying balloon expansion process, where the dosage, the pressure of application, and the selection of the medication may be independently made apart from the balloon expansion process.

DESCRIPTION OF SPECIFIC EMBODIMENTS

Figure 1:
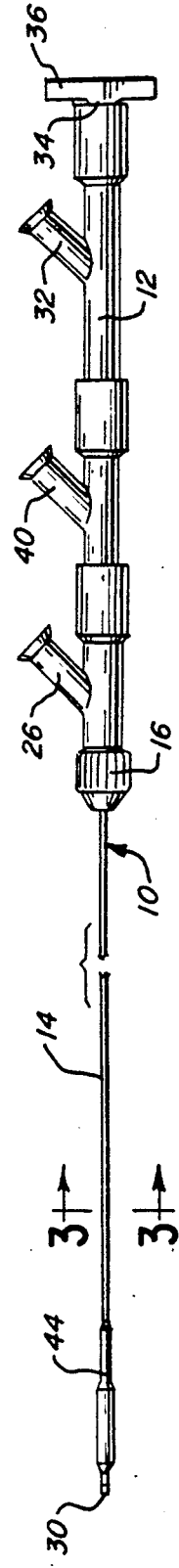
FIG. 1 is a plan view of the catheter of this invention.
Figure 4:
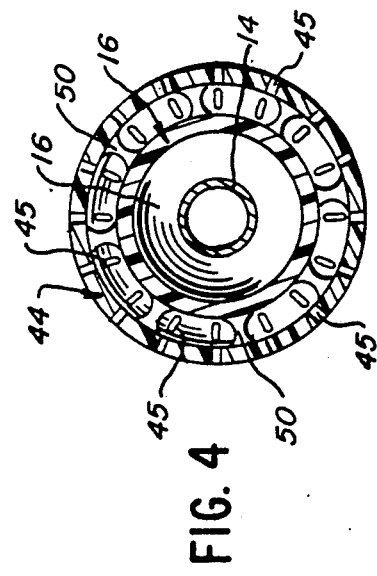
FIG. 4 is a sectional view taken along line 4—4 of FIG. 2.

Referring to the drawings, a balloon-type catheter is disclosed, being similar in purpose and construction to a commercially available PTCA dilatation catheter except as otherwise shown.

As is conventional, proximal catheter hub 12 is provided, being typically made of a rigid polycarbonate material. At the distal end of hub 12 is attached catheter tubing 14 which may be made of nylon, for example, being attached to hub 12 by manifold 16 of conventional design.

Figure 3:
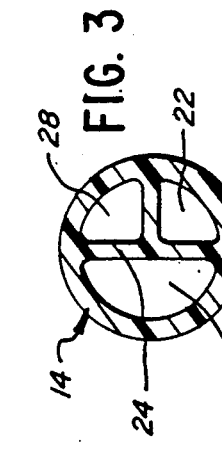
FIG. 3 is a sectional view taken along line 3—3 of FIG. 1.

At the distal end of catheter tube 14 is positioned a pair of catheter balloons in generally telescoping relation with each other. A first inner balloon 16 is a conventional PTCA inflation balloon made of nylon, heat sealed at its respective ends 18 to the outside of catheter tubing 14. One or more inflation ports 20 pass through the wall of catheter body 14 to provide communication between the interior of first balloon 16 and a catheter lumen 22, shown in cross section in FIG. 3 as being defined by an integral, T-shaped interior wall 24 of catheter 14. Lumen 22 communicates with inflation port 20 at the distal end and with inflation port 26 near the proximal end of the catheter. Inflation port 26 provides temporary sealing communication with a syringe or any other desired source of compressed fluid in a manner conventional for balloon catheters.

Another lumen 28 is provided within catheter body 14. Lumen 28 extends completely through the catheter, forming an open aperture at the distal end 30 at one end and communicating with lateral injection port 32 close to the proximal end 34. Additionally, lumen 28 communicates axially completely through hub 12 to extend through the proximal end 34 of the catheter as well. A conventional hemostasis screw 36 may be threadedly attached to the proximal end 34 of the catheter, to close off and seal the proximal end of lumen 28.

Thus, a guide wire may be inserted through the entire length of lumen 28 of the catheter, to assist in catheter insertion in conventional manner. Then, after the catheter has been inserted to the desired position, the guide wire may be removed, and the hemostasis screw 36 applied. At this point, X-ray contrast or other desired solution may be administered through port 32, from where it is conveyed through the catheter and out of distal end 30.

In accordance with this invention, another lumen 38 is provided to catheter body 14, identified as the "second lumen" herein. Lumen 38 communicates at its proximal end with lateral connection port 40, and at its distal end with one or more lateral ports 42 positioned in catheter body 14 typically proximally to balloon 16. A second balloon 44 is carried by catheter body 14, the second balloon being positioned generally radially outwardly about first balloon 16 in telescoping relation therewith. However, in this embodiment, a portion 43 of second balloon 44 is positioned proximally of first balloon 16 to provide for communication of port 42 with the space 47 between the first and second balloons 44, 16. Second balloon 44 may be made, for example, of poly(ethylene terephthalate) or nylon.

As previously described, second balloon 44 defines aperture means in the form of holes 45, typically in the form of pores or perforations, of dimensions and types described above. Typically, second balloon 44 will be made of the same material as catheter body 14 to facilitate good heat seals 46 between second balloon 44 and catheter body 14. The distal heat seal 46 may be placed on top of heat seal 18, if desired.

It is preferred for a large plurality of spaced apertures 45 to be distributed about substantially the entire surface of second balloon 44 to maximize the uniformity of distribution of whatever medication passes outwardly through the wall of second balloon 44.

Such balloons 44 may be made by a variety of processes, for example by laser punching of holes in a preformed plastic balloon, or by punching with multiple needles on a platen or jig, or making use of a slitting machine to form a multiplicity of slits about the surface area of the balloon. Alternatively, porous plastic tubing may be extruded by means of a variety of processes involving a two component system homogenous liquid is cooled to form a two phase, immiscible liquid system, following which the extruded mixture is quickly cooled to form a two phase solid matrix. Following this, one of the phases is washed out of the system, leaving a porous tube. Such processes are well-known to the art.

Accordingly, the catheter of this invention, after insertion into a body cavity such as a coronary artery, may be used by inflating the first balloon 16 in a conventional PTCA process to enlarge the lumen of an artery which is partially blocked by a stenosis. The pressurized fluid for this process is provided to first balloon 16 through inflation port 26 and lumen 22.

Also, either before, during, or after the process of inflating balloon 16, medications such as heparin solution or any other desired medication or mixtures thereof may be administered through port 40 and lumen 38 into the space 47 between balloons 16 and 44. Pressure may be applied as necessary, either directly through port 40 or indirectly by the inflation of balloon 16, causing the medication to migrate outwardly through the wall of the balloon 44 to the surrounding tissue.

It can be seen that the catheter of this invention provides great versatility in that pressure without medication can be applied, or medication can be applied with pressure, and also medication can be applied without significant pressure, with sequential administrations of different kinds of medication being available, and last minute choices may be made as to the medication to be administered. All of this is possible with the insertion of a single catheter. Likewise, medication which is incompatible in some way with the fluid used to inflate balloon 16 may be provided in a separated manner, and also the medication may be kept relatively separate, at least until delivery, from X-ray contrast media or the like administered to lumen 28 through port 32.

Figure 2:
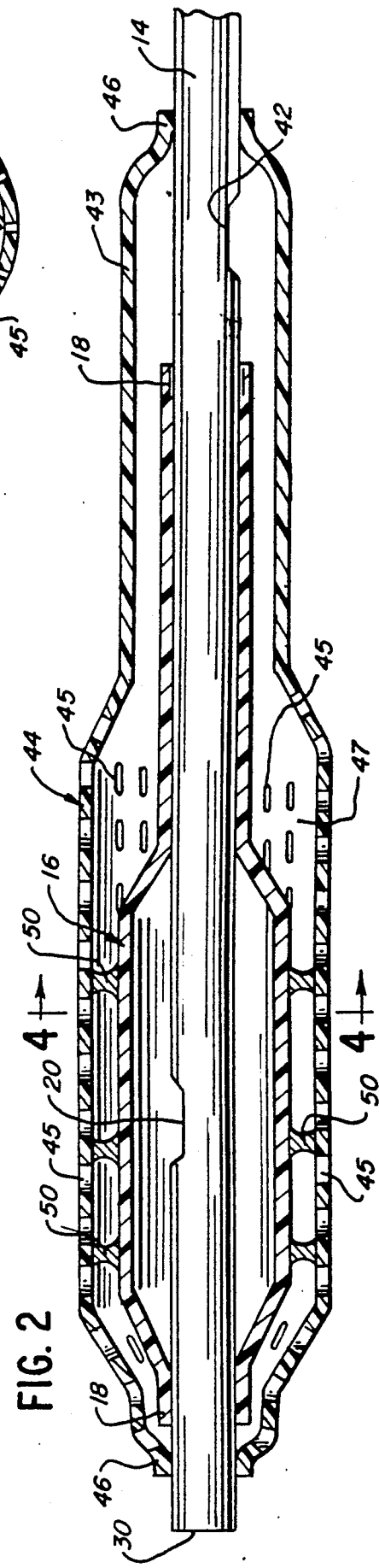
FIG. 2 is an enlarged, fragmentary, longitudinal sectional view of the distal tip of the catheter of FIG. 1.

It may also be desirable to connect the respective balloon 16, 44 with thin, spaced spot seals 50 so that balloon 44 is retracted as balloon 16 is retracted, but a substantial space 47 still remains between the two balloons to receive medication. The thickness of spot seals 50 and the spacing between balloon 16, 44 is exaggerated in FIG. 2 for purposes of clear illustration.

An advantage of spot seals 50 comes particularly in the preparation of the catheter for insertion into the body. Typically, balloon catheters have their balloons completely collapsed by application of a suction pressure to their lumen, so that the balloon initially assumes the smallest possible cross-sectional dimension. However, because of the presence of apertures 45 in second balloon 44, it is not easily collapsed by suction, particularly when many apertures are present as may be desirable, or the apertures have a dimension larger than 0.0005 inch or so. Accordingly, the presence of spot seals 50 causes second balloon 44 to collapse with first balloon 16. Further collapse of balloon 44 may be achieved to a certain extent with a substantial suction that can take air out of the balloon faster than it enters through apertures 45. Additionally, if desired, outer balloon may be wrapped in an impermeable wrapping to assist in the suction collapse.

Figure 5:
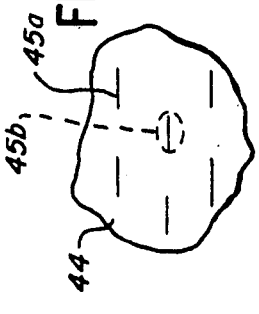
FIG. 5 is an enlarged, fragmentary plan view of a portion of the outer balloon of the catheter of FIG. 1, showing slit-type apertures as an alternate embodiment.

Referring to FIG. 5, a section of outer balloon 44 is shown as an alternate embodiment in which the apertures 45a are of a slit-type, normally having abutting sides. However, under pressure the slits open as shown at dotted line reference numeral 45b, for flow communication.

The above has been offered for illustrative purposes only, and is not intended to limit the scope of the invention of this application, which is as defined in the claims below.

That which is claimed is:

1. In a balloon catheter which comprises a catheter shaft which defines a first inflation lumen and a first, inflatable balloon mounted on said shaft in communication with said first inflation lumen, the improvement comprising, in combination:

a second inflation lumen, spaced from said first lumen, defined by said catheter shaft, and a second balloon mounted on said shaft in communication with said second inflation lumen, said second balloon defining aperture means sized to permit liquid flow outwardly through said second balloon, whereby medication may be delivered in controlled manner, said second balloon being spot-sealed to said first balloon in a plurality of spaced areas which are spaced from the ends of said balloons.

2. The balloon catheter of claim 1 in which said aperture means comprises slits in the second balloon wall having abutting sides in their normal, unstretched configuration.

3. The catheter of claim 3 in which said second balloon is positioned generally radially outwardly about said first balloon in telescoping relation therewith.

4. The catheter of claim 1 in which said catheter shaft defines a third lumen for receiving a guide wire.

5. The balloon catheter of claim 1 in which said aperture means comprises holes having a diameter of 0.01 to 0.05 inch.

6. The balloon catheter of claim 1 in which said second balloon is made of poly(ethylene terephthalate) or nylon.

7. In a balloon catheter which comprises a catheter shaft which defines a first inflation lumen and a first, inflatable balloon mounted on said shaft in communication with said first inflation lumen, the improvement comprising, in combination:

a second inflation lumen spaced from said first lumen, defined by said catheter shaft, and a second balloon mounted on said shaft in communication with said second inflation lumen, said second balloon defining apertures sized to permit liquid flow outwardly through said second balloon, said second balloon being positioned generally radially outwardly about said first balloon in telescoping relation therewith, said apertures comprising slits in said second balloon wall having abutting sides in their normal, unstretched configuration, whereby medication may be delivered in controlled manner, said second balloon being spot-sealed to said first balloon in a plurality of spaced areas which are spaced from the ends of said balloons.

8. The catheter of claim 7 in which said catheter shaft defines a third lumen for receiving a guide wire.

9. The balloon catheter of claim 8 in which said second balloon is made of poly(ethylene terephthalate) or nylon.

10. In the method of expanding a partially occluded artery which comprises inserting a catheter shaft having an inner balloon carried thereon into said artery and inflating said balloon to expand the lumen of said artery, the improvement comprising, in combination:

a second, outer balloon being positioned about said inner balloon and spot-sealed to said inner balloon in a plurality of spaced areas which are spaced from the ends of said balloons, and including the steps of, prior to inserting said catheter shaft and inner and second balloons into said artery, applying suction to the interior of said inner balloon to collapse both it and the second balloon spot-sealed thereto, and, after inserting said catheter shaft and inner and second balloons into said artery, pressurizing said inner balloon to expand the lumen of said artery, and conveying medication through a catheter lumen to a space between the exterior of said inner balloon and said second, outer balloon positioned bout said inner balloon, and thereafter passing said medication through aperture means in said second outer balloon to provide medication to a site of stenosis in the artery in a manner correlated with the process of expanding the lumen of said artery.

11. The method of claim 10 in which the inner balloon is pressurized to expand the lumen of said artery simultaneously with the step of providing medication to the space between the inner and outer balloon, whereby said medication passes through the apertures of said outer balloon under pressure, to be forced into said stenosis site.

12. The method of claim 10 in which the pressure applied to said inner balloon is released, followed by administration of said medication to the space between the inner and outer balloons, whereby medication passes to said stenosis site through said apertures.

13. The method of claim 12 in which said inner balloon is again pressurized as said medication reaches the stenosis site, to force said medication into the stenosis site by expansion of said balloons.

* * * * *